US00PP08410P

United States Patent [19]

Guillen

[11] Patent Number: Plant 8,410

[45] Date of Patent: Oct. 5, 1993

[54] NEW GUINEA IMPATIENS NAMED BSR-203 PURE WHITE

[75] Inventor: Mario Guillen, Cartago, Costa Rica

[73] Assignee: George J. Ball, Inc., West Chicago, Ill.

[21] Appl. No.: 917,274

[22] Filed: Jul. 23, 1992

[51] Int. Cl.[5] ..... A01H 5/00

[52] U.S. Cl. ..... Plt./87.6

[58] Field of Search ..... Plt./87.6

*Primary Examiner*—James R. Feyrer

*Attorney, Agent, or Firm*—Burns, Doane, Swecker & Mathis

[57] ABSTRACT

A new and distinct New Guinea Impatiens cultivar named BSR-203 Pure White is provided. This new cultivar was the result of a controlled breeding program wherein a plant designated N1502-1 (nonpatented in the United States) was pollinated by the Milkyway cultivar (U.S. Plant Pat. No. 5,125). The new cultivar forms attractive clear white blossoms combined with a strong basal branching character and a compact mounded growth habit and can be readily distinguished from the Jasius cultivar (U.S. Plant Pat. No. 7,345).

1 Drawing Sheet

SUMMARY OF THE INVENTION

The present invention comprises a new and distinctive Impatiens plant, botanically known as New Guinea Impatiens, and hereafter referred to by the cultivar name BSR-203 Pure White.

The new cultivar is the product of a planned breeding program. More specifically, the breeding program which resulted in the production of the new cultivar was carried out in a controlled environment during 1988 at Linda Vista, Cartago, Costa Rica. The female parent (i.e., the seed parent) was a plant designated N1502-1 (nonpatented in the United States) which exhibits white medium-sized blossoms with green foliage. The male parent (i.e., the pollen parent) was the Milkyway cultivar (U.S. Plant Pat. No. 5,125) which exhibits white medium-sized blossoms with variegated green foliage. The parentage of the new cultivar can be summarized as follows:

N1502-1 × Milkyway.

The seeds resulting from the above pollination were sown and plantlets were obtained which were physically and biologically different from each other. Selective study resulted in the identification of a single plant of the new cultivar. This plant had dark pink blossoms and initially was designated BSR-203.

It was found that the cultivar of the present invention:

(a) exhibits attractive pure white blossoms which commonly measure approximately 6.0 cm. in diameter and approximately 5.75 cm. in length,
(b) exhibits a strong basal branching character, and
(c) exhibits a compact mounded growth habit.

Asexual reproduction of the new cultivar by terminal or stem cuttings taken during February, 1990 at Santa Maria, Calif., U.S.A., has demonstrated that the characteristics of the new cultivar as herein described are firmly fixed and are retained through successive generations of such asexual propagation.

The BSR-203 Pure White cultivar has not been observed under all possible environmental conditions to date. Accordingly, it is possible that the phenotype may vary somewhat with variations in the environment, such as temperature, light intensity, and day length.

When the new cultivar of the present invention is compared to the Jasius cultivar (U.S. Plant Pat. No. 7,345), it is found that the new cultivar is more compact and better branched than the Jasius cultivar and exhibits a compact mounded growth habit. The flowers of the new cultivar are larger and of a purer white appearance than those of the Jasius cultivar. For instance, the flowers of the Jasius cultivar commonly measure approximately 5.0 cm. in diameter and approximately 5.25 cm. in length and commonly exhibit a light green tint. Also, the foliage of the new cultivar tends to be broader and less glossy than that of the Jasius cultivar.

When plant material of the BSR-203 Pure White cultivar is subjected to standard random amplified polymorphic DNA marker analysis (RAPD) using polymerase chain reaction (PCR) and a known unique set of DNA primers, it is found to exhibit a different fingerprint map when compared to that of the Jasius cultivar which confirms its genetic distinctiveness.

Plants of the new cultivar will be marketed under the Celebration trademark by George J. Ball, Inc.

BRIEF DESCRIPTION OF THE PHOTOGRAPH

The accompanying photograph shows as nearly true as it is reasonably possible to make the same in a color illustration of this character, a typical specimen of an overall plant of the new cultivar. The plant was grown in a greenhouse at Arroyo Grande, Calif., U.S.A.

DETAILED DESCRIPTION

The chart used in the identification of colors described herein is the R.H.S. Colour Chart of The Royal Horticultural Society, London, England. The color values were determined at Arroyo Grande, Calif., U.S.A. during the first week of January, 1992. The plants were produced from cuttings taken from stock plants and were grown under standard greenhouse conditions comparable to those used in commercial practice while utilizing a soilless growth medium and maintaining temperatures of approximately 72° F. during the day and approximately 65° F. during the night.

Propagation:

*Type cutting.*—Terminal tip.

*Time to initiate roots.*—Approximately 14 to 21 days with the shorter times generally being experienced in the summer and the longer times in the winter.

*Rooting habit.*—Fibrous and branching.

Plant description:

*Form.*—Strong basal branching.

*Habit of growth.*—Compact and mounded. A mature plant commonly measures approximately 12 inches in height and approximately 15 inches in width.

*Foliage.*—The configuration is narrow and lanceolate. The leaves of the BSR-203 Pure White cultivar measure approximately 8 cm.×3.25 cm. while those of the Jasius cultivar measure approximately 11.0 cm.×2.75 cm. The foliage of the BSR-203 Pure White cultivar is Green Group 137A (abaxial) and Green Group 137D (adaxial). This can be compared to Green Group 141A (abaxial) and Green Group 141A (adaxial) for the Jasius cultivar. The foliage of the new cultivar is duller in appearance and less glossy than that of the Jasius cultivar. The stem color is Green Group 143B with a hint of Red Group 53A while that of the Jasius cultivar is Green Group 143C with a hint of Red Group 46A.

Flower description:

*Flowering habit.*—Freely flowering.

*Natural flowering season.*—Year-round in greenhouse environment.

*Flowers Borne.*—Above foliage, arising from leaf axils.

*Flower color.*—Pure white, White Group 155D (abaxial and adaxial). This can be compared to a more cream white, White Group 155B, with a light green tint (abaxial and adaxial) for the Jasius cultivar.

*Quantity of flowers.*—Approximately 5 to 10 per stem.

*Number of petals.*—Five.

*Flower diameter.*—Approximately 6.0 cm. which can be compared to approximately 5.0 cm. for the Jasius cultivar.

*Nectary length.*—Approximately 5.0 cm. which can be compared to approximately 4.75 cm. for the Jasius cultivar.

*Reproductive organs.*—The anthers are fused together forming one organ that surrounds the pistil. Generally, the anthers shed pollen prior to the stigma becoming receptive. The pollen color is cream-white, White Group 155D. The stigma color is White Group 155D and can be compared to White Group 155D exhibited by the Jasius cultivar. The ovary color is Yellow-Green Group 146A and can be compared to Yellow-Green Group 146A exhibited by the Jasius cultivar.

I claim:

1. A new and distinct cultivar of New Guinea Impatiens named BSR-203 Pure White, substantially as herein shown and described, which:

(a) exhibits attractive pure white blossoms which commonly measure approximately 6.0 cm. in diameter and approximately 5.75 cm. in length, (b) exhibits a strong basal branching character, and (c) exhibits a compact mounded growth habit.

* * * * *

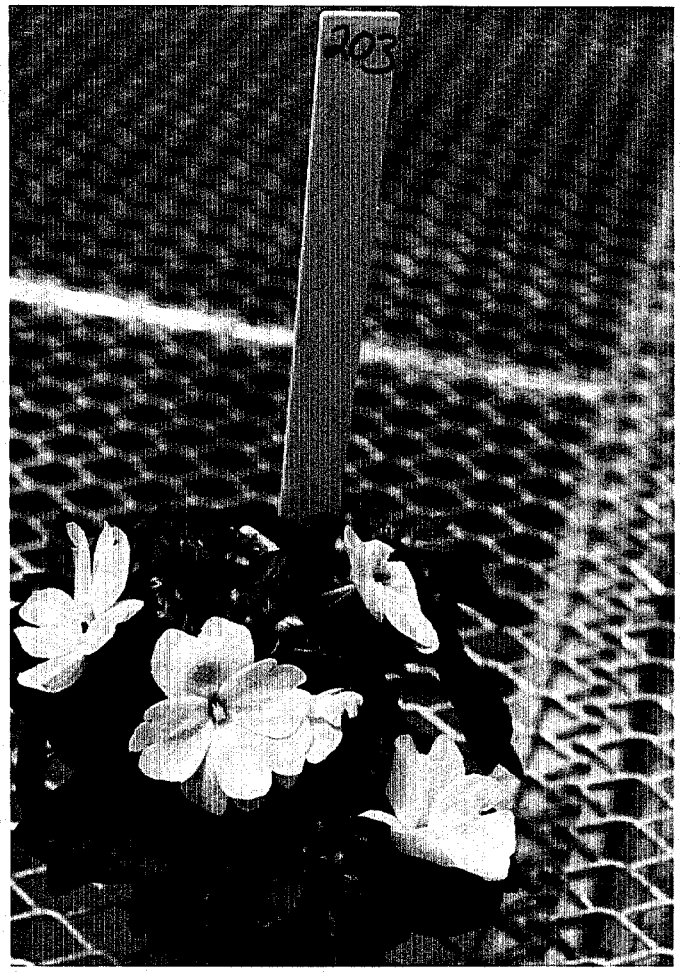
203